US010584092B2

(12) United States Patent
Shinkai et al.

(10) Patent No.: US 10,584,092 B2
(45) Date of Patent: Mar. 10, 2020

(54) METHOD FOR PRODUCING AROMATIC NITRILE COMPOUND AND METHOD FOR PRODUCING CARBONATE ESTER

(71) Applicants: MITSUBISHI GAS CHEMICAL COMPANY, INC., Chiyoda-Ku (JP); TOHOKU UNIVERSITY, Sendai-Shi (JP); NIPPON STEEL & SUMITOMO METAL CORPORATION, Chiyoda-Ku (JP); NIPPON STEEL ENGINEERING CO., LTD., Shinagawa-Ku (JP)

(72) Inventors: Yousuke Shinkai, Tokyo (JP); Hongyu Liu, Tokyo (JP); Hidefumi Harada, Tokyo (JP); Yoshinori Isahaya, Tokyo (JP); Keiichi Tomishige, Miyagi (JP); Yoshinao Nakagawa, Miyagi (JP); Masazumi Tamura, Miyagi (JP); Kimihito Suzuki, Tokyo (JP); Yasuki Namiki, Tokyo (JP)

(73) Assignees: MITSUBISHI GAS CHEMICAL COMPANY, INC., Tokyo (JP); TOHOKU UNIVERSITY, Miyagi (JP); NIPPON STEEL CORPORATION, Tokyo (JP); NIPPON STEEL ENGINEERING CO., LTD., Tokyo (JP)

( * ) Notice: Subject to any disclaimer, the term of this patent is extended or adjusted under 35 U.S.C. 154(b) by 0 days.

(21) Appl. No.: 16/310,210

(22) PCT Filed: Jun. 20, 2017

(86) PCT No.: PCT/JP2017/022602
§ 371 (c)(1),
(2) Date: Dec. 14, 2018

(87) PCT Pub. No.: WO2017/221908
PCT Pub. Date: Dec. 28, 2017

(65) Prior Publication Data
US 2019/0185408 A1  Jun. 20, 2019

(30) Foreign Application Priority Data
Jun. 22, 2016  (JP) .................................. 2016-123945

(51) Int. Cl.
| | | |
|---|---|---|
| *C07C 68/04* | (2006.01) | |
| *C07C 69/96* | (2006.01) | |
| *C07D 213/84* | (2006.01) | |
| *C07D 241/24* | (2006.01) | |
| *C07B 61/00* | (2006.01) | |

(52) U.S. Cl.
CPC .............. *C07C 68/04* (2013.01); *C07C 69/96* (2013.01); *C07D 213/84* (2013.01); *C07D 241/24* (2013.01); *C07B 61/00* (2013.01); *Y02P 20/142* (2015.11)

(58) Field of Classification Search
CPC ....... C07C 68/04; C07C 69/96; C07D 241/24; C07D 213/84; Y02P 20/142; C07B 61/00
See application file for complete search history.

(56) References Cited

U.S. PATENT DOCUMENTS

| | | | |
|---|---|---|---|
| 3,106,568 A | 10/1963 | Spaeth et al. | |
| 10,138,183 B2 * | 11/2018 | Rinker | ...................... C07C 7/20 |
| 2005/0203307 A1 * | 9/2005 | Ryu | ........................ C07C 68/00 |
| | | | 558/277 |

FOREIGN PATENT DOCUMENTS

| | | |
|---|---|---|
| JP | 61-161276 A | 7/1986 |
| JP | 11-240947 A | 9/1999 |
| JP | 2010-77113 A | 4/2010 |
| JP | 2012-162523 A | 8/2012 |
| WO | 2015/099053 A | 7/2015 |
| WO | WO-2015099053 A1 * | 7/2015 ............. C07C 68/04 |

OTHER PUBLICATIONS

IUPAC Compendium on Chemical Technology Version 2.3.3 (2014) p. 214.*
WO-2015099053-A1; WIPO English machine translation (2015); p. 1-151.*
Zhang, L. et al., "Chinese Journal of Pharmaceuticals", 2007, pp. 477-478, vol. 38 (7).
Rao, S. et al., "Indian Journal of Chemistry", 1989, pp. 918-922, vol. 28B.
Honda, M. et al., "Journal of Catalysis", 2014, pp. 95-107, vol. 318.
International Search Report issued in Patent Application No. PCT/JP2017/022602, dated Aug. 8, 2017.
International Preliminary Report on Patentability in Patent Application No. PCT/JP2017/022602, dated Dec. 25, 2018.

(Continued)

*Primary Examiner* — John M Mauro
(74) *Attorney, Agent, or Firm* — Greenblum & Bernstein, P.L.C.

(57) ABSTRACT

Provided is a method for regenerating an aromatic amide compound into a corresponding aromatic nitrile compound, the method realizing a dehydration reaction of providing a target compound selectively at a high yield with generation of a by-product being suppressed. Also provided is a method for producing an aromatic nitrile compound that decreases the number of steps of dehydration reaction and significantly improves the reaction speed at a pressure close to normal pressure. Furthermore, the above-described production method is applied to a carbonate ester production method to provide a method for producing carbonate ester efficiently. The above-described objects are achieved by a method for producing an aromatic nitrile compound including a dehydration reaction of dehydrating an aromatic amide compound, in which the dehydration reaction uses diphenylether.

15 Claims, 3 Drawing Sheets

(56) References Cited

OTHER PUBLICATIONS

Extended European Search Report (EESR) dated Oct. 23, 2019 in corresponding EP patent application No. 17815376.3.
Enthaler et al., "Copper-Catalyzed Dehydration of Primary Amides to Nitriles," Catal Lett (2011) 141:1079-1085.
Enthaler, "Straightforward Uranium-Catalyzed Dehydration of Primary Amides to Nitriles," Chem. Eur. J. (2011) 17, 9316-9319.
Sueoka et al., "Supported Monomeric Vanadium Catalyst for Dehydration of Amide to Form Nitriles," Chem. Commun. (2010) 46, 8243-8245.

\* cited by examiner

METHOD FOR PRODUCING AROMATIC NITRILE COMPOUND AND METHOD FOR PRODUCING CARBONATE ESTER

TECHNICAL FIELD

The present invention relates to a method for producing an aromatic compound such as cyanopyridine, cyanopyrazine or the like, and a method for producing a carbonate ester.

BACKGROUND ART

"Carbonate ester" is a generic name of a compound obtained as a result of one atom or two atoms among two hydrogen atoms of carbonic acid, $CO(OH)_2$, being substituted with an alkyl group or an aryl group, and has a structure of RO—C(=O)—OR (R and R' each represent a saturated hydrocarbon group or an unsaturated hydrocarbon group).

A carbonate ester is used as an additive, for example, a gasoline additive for improving the octane value and a diesel fuel additive for decreasing the amount of particles in exhaust gas. A carbonate ester is also used as, for example, an alkylation agent, a carbonylation agent, a solvent or the like usable for synthesizing resins or organic compounds such as polycarbonate, urethane, pharmaceutical drugs, agricultural chemicals or the like, a material of an electrolytic solution of lithium ion cells, a material of lubricant oil, or a material of an oxygen absorber for rust inhibition of boiler pipes. As can be seen, a carbonate ester is a very useful compound.

According to a conventionally mainstream method for producing a carbonate ester, phosgene, which is used as a source of a carbonyl, is directly reacted with an alcohol. Phosgene used in this method is highly hazardous and highly corrosive, and therefore, needs extreme caution to be handled, for example, transported or stored. It is highly costly to control and manage, and guarantee the safety of, production facilities of phosgene. According to this method, the materials and catalysts used for producing a carbonate ester contain halogen such as chlorine or the like, and the produced carbonate ester contains a trace amount of halogen, which is not removed by a simple purification step. When the carbonate ester is used for a gasoline additive, a light oil additive or an electronic material, such halogen may undesirably cause corrosion. Therefore, a thorough purification step is indispensable to decrease the trace amount of halogen in the carbonate ester to the level of an extremely trace amount. In addition, recently, administrative offices provide a strict administration guidance and do not permit new establishment of production facilities using this method because phosgene is highly hazardous to the human body. In such a situation, a new production method of a carbonate ester that does not use phosgene is strongly desired.

There is another known method for producing a carbonate ester. According to this method, a carbonate ester is directly synthesized from an alcohol and carbon dioxide using a heterogeneous catalyst. Regarding this method, studies had been on using 2-cyanopyridine or benzonitrile as a wettable powder to significantly improve the production amount and the production speed of the carbonate ester, to allow the reaction to advance easily at a pressure close to normal pressure, and to increase the reaction speed (see Patent Documents 1 and 2). However, there was a problem regarding the method for treating or using benzamide or the like generated as a by-product.

For example, the use of benzamide generated by the reaction of benzonitrile and water is limited to being for some of pharmaceutical and agrochemical intermediates. Therefore, regarding the method of producing a carbonate ester using benzonitrile as a wettable powder, benzamide generated as a by-product is desired to be regenerated into benzonitrile and reused. It is now an issue to realize a regeneration reaction with a high level of selectivity (because it is considered that if a by-product is generated, benzonitrile is not easily used as a wettable powder) and a high yield (because if the yield is low, benzamide remains in a large amount, which increases the amount of work, namely, work load, of separating benzamide and benzonitrile from each other).

In light of the above-described situation where regeneration of benzamide or the like into benzonitrile or the like involves problems, there is a known method for realizing the regeneration with no use of a strong reagent and with the generation of a by-product being suppressed (Patent Document 3).

However, according to this method, generation of nitrile by dehydration of an amide compound requires 400 hours and thus is not well balanced to be adopted with a carbonate ester synthesis reaction, which requires only 24 hours. This method also has a problem that steps of extraction, infiltration and the like are necessary for solid-liquid separation of a catalyst, which increases the number of production steps and complicates the production process.

CITATION LIST

Patent Literature

Patent Document 1: Japanese Laid-Open Patent Publication No. 2010-77113
Patent Document 2: Japanese Laid-Open Patent Publication No. 2012-162523
Patent Document 3: WO2015/099053

SUMMARY OF INVENTION

Technical Problem

In light of the above-described technological problems, an object of the present invention is to provide a method for regenerating an aromatic amide compound, for example, pyridine carboamide or pyrazine amide, into a corresponding aromatic nitrile compound, namely, cyanopyridine or cyanopyrazine, the method realizing a dehydration reaction of providing a target compound selectively at a high yield, with generation of a by-product being suppressed. Another object of the present invention is to provide a method for producing an aromatic nitrile compound that decreases the number of steps of the dehydration reaction and significantly improves the reaction speed to shorten the reaction time even at a pressure close to normal pressure.

A still another object of the present invention is to apply the above-described production method of the aromatic nitrile compounds to a carbonate ester production method to provide a method for producing a carbonate ester efficiently.

Solution to Problem

In order to achieve the above-described objects, the present inventors made studies on a method for producing an aromatic nitrile compound such as cyanopyridine, cyanopyrazine or the like by dehydration of an aromatic amide compound. More specifically, the present inventors studied reaction conditions for dehydrating an aromatic amide compound, and as a result, found the following. In the case where diphenylether having a boiling point higher than that of the aromatic nitrile compound to be generated and lower than that of the aromatic amide compound as the material is used, and the reaction temperature is adjusted, a process of dehydration reaction is realized by which the reaction speed is significantly improved to shorten the reaction time, the target compound is obtained selectively at a high yield while generation of a by-product is suppressed, and the aromatic nitrile compound is easily recovered. The present inventors also found the following. Since the process of dehydration reaction conceived by the present inventors does not need to perform solid-liquid separation of a catalyst, the number of steps of the dehydration reaction is decreased. Preferably, the dehydration reaction is advanced in a state where diphenylether is boiled.

As a result of the above, the speed of regenerating an aromatic nitrile compound by a dehydration reaction of an aromatic amide compound, and the speed of synthesizing a carbonate ester from $CO_2$ and an alcohol using the aromatic nitrile compound, are now well balanced. Namely, the dehydration reaction and the carbonate ester synthesis reaction are now established as a series of commercial processes. Based on this, the present inventors also made studies on applying the above-described knowledge to a method for producing a carbonate ester. Namely, the present inventors have found the following regarding the carbonate ester production method of directly synthesizing a carbonate ester from an alcohol and carbon dioxide. In the case where a solvent having a boiling point higher than that of the aromatic amide compound is used, the number of steps of the reaction is decreased and the method is simplified with no need of solid-liquid separation of a catalyst. The present inventors have confirmed that such a carbon ester synthesis method may be combined with the dehydration reaction of an aromatic amide compound to generate an aromatic nitrile compound, so that a splendid effect is provided. The gist of the present invention is as follows.

(1) A method for producing an aromatic nitrile compound, comprising:
a dehydration reaction of dehydrating an aromatic amide compound;
wherein the dehydration reaction uses diphenylether.

(2) The method for producing an aromatic nitrile compound according to (1) above, wherein the dehydration reaction is performed in a state where diphenylether is boiled.

(3) The method for producing an aromatic nitrile compound according to (2) above, wherein the diphenylether has a boiling point that is higher than the boiling point of the aromatic nitrile compound and the boiling point of water and lower than the boiling point of the aromatic amide compound.

(4) The method for producing an aromatic nitrile compound according to any one of (1) through (3) above, wherein the dehydration reaction is performed at a reduced pressure.

(5) The method for producing an aromatic nitrile compound according to any one of (1) through (4) above, wherein a reaction solution of the dehydration reaction has a temperature that is 170° C. or higher and lower than 230° C.

(6) The method for producing an aromatic nitrile compound according to any one of (1) through (5) above, wherein the aromatic amide compound contains pyridine carboamide or pyrazine amide, and the aromatic nitrile compound contains cyanopyridine or cyanopyrazine.

(7) The method for producing an aromatic nitrile compound according to any one of (1) through (6) above, wherein the dehydration reaction uses a catalyst containing cesium.

(8) A method for producing a carbonate ester, comprising:
a first reaction step including a carbonate ester generation reaction of reacting an alcohol and carbon dioxide in the presence of an aromatic nitrite compound to generate a carbonate ester and water, and a hydration reaction of hydrating the generated water to the aromatic nitrile compound to generate an aromatic amide compound; and
a second reaction step of, after the aromatic amide compound is separated from a reaction system of the first reaction step, regenerating the aromatic amide compound into the aromatic nitrile compound by a dehydration reaction of dehydrating the aromatic amide compound at a temperature of a reaction solution of 170° C. or higher and lower than 230° C.;
wherein at least a part of the aromatic nitrile compound regenerated in the second reaction step is used in the first reaction step.

(9) A method for producing a carbonate ester, comprising:
a first reaction step including a carbonate ester generation reaction of reacting an alcohol and carbon dioxide in the presence of an aromatic nitrile compound to generate a carbonate ester and water, and a hydration reaction of hydrating the generated water to the aromatic nitrile compound to generate an aromatic amide compound; and
a second reaction step of, after the aromatic amide compound is separated from a reaction system of the first reaction step, regenerating the aromatic amide compound into the aromatic nitrile compound by a dehydration reaction of dehydrating the aromatic amide compound in the presence of diphenylether;
wherein at least a part of the aromatic nitrile compound regenerated in the second reaction step is used in the first reaction step.

(10) The method for producing a carbonate ester according to (8) or (9) above, wherein the aromatic amide compound contains pyridine carboamide or pyrazine amide, and the aromatic nitrile compound contains cyanopyridine or cyanopyrazine.

(11) The method for producing a carbonate ester according to any one of (8) through (10) above, wherein the dehydration reaction uses a catalyst containing cesium.

(12) The method for producing a carbonate ester according to any one of (8) through (11) above, wherein the carbonate ester generation reaction uses a catalyst containing cesium.

(13) The method for producing a carbonate ester according to any one of (8) through (12) above, wherein the alcohol contains an alcohol having a carbon number of 1 to 6.

(14) The method for producing a carbonate ester according to any one of (8) through (13) above, wherein the first reaction step uses a solvent having a boiling point higher than the boiling point of the aromatic amide compound to be generated.

(15) The method for producing a carbonate ester according to (14) above, wherein the solvent contains at least one of dialkylbenzene, alkylnaphthalene, and diphenylbenzene.

Advantageous Effects of Invention

According to the present invention as described above, an aromatic nitrile compound such as cyanopyridine, cyanopyrazine or the like is efficiently produced (regenerated) from an aromatic amide compound such as pyridine carbonamide (picolinamide, nicotinamide or the like), benzamide or the like. More specifically, the dehydration reaction of an aromatic amide compound for the regeneration is performed to obtain a target compound selectively at a high yield, while generation of a by-product is suppressed. Even under mild reaction conditions, for example, at a pressure close to normal pressure, the reaction speed is increased. Therefore, according to the present invention, the reaction time of the dehydration reaction of regenerating an aromatic nitrile compound is significantly shortened as compared with the reaction time required by the conventional method.

Also according to the present invention, an aromatic nitrile compound is produced as described above, and as a result, a method for producing a carbonate ester efficiently is realized.

DESCRIPTION OF EMBODIMENTS

Figure 1:
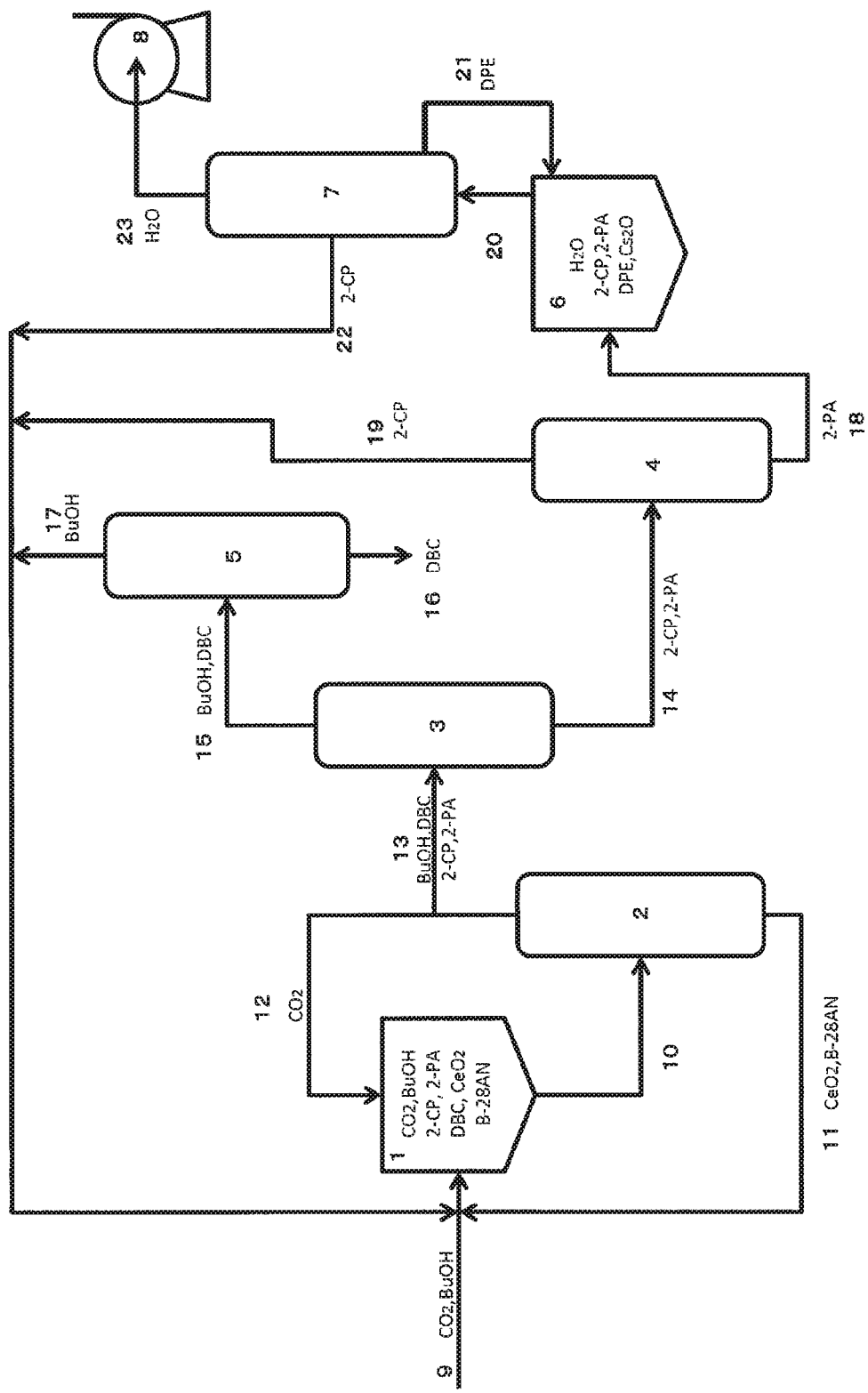
FIG. 1 shows an example of device for producing a carbonate ester.

Hereinafter, a preferred embodiment of the present invention will be described in detail with reference to the attached drawings. In the specification and the drawings, components having substantially the same functions or structures will bear the same reference signs, and the same descriptions will not be repeated.

<1. Method for Producing an Aromatic Nitrile Compound>

According to a method of the present invention for producing an aromatic nitrile compound, an aromatic nitrile compound such as cyanopyridine, cyanopyrazine or the like is produced by dehydration of an aromatic amide compound such as pyridine carboamide (2-pyridine carboamide, 3-pyridine carboamide or 4-pyridine carboamide), pyrazine amide or the like. According to this method, an aromatic amide compound is subjected to a dehydration reaction in the presence of, for example, a catalyst containing a basic metal oxide and diphenylether to generate an aromatic nitrile compound.

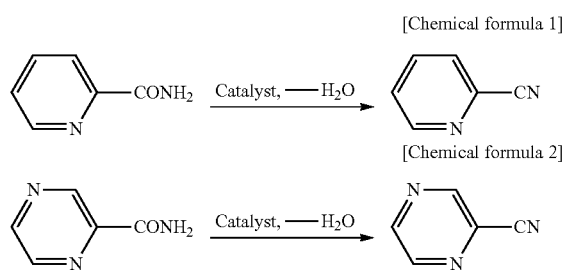

[Chemical formula 1]

[Chemical formula 2]

The catalyst usable in the above-described dehydration reaction according to the present invention contains an oxide of an alkaline metal (K, Li, Na, Rb, Cs), which is basic. Preferably, the catalyst usable in the above-described reaction contains an oxide of at least one of Na, K, Rb and Cs. A carrier of the catalyst may be a substance that generally acts as a carrier of a catalyst. As a result of studies made on various carriers, it has been found that the catalyst exhibits an especially high level of performance when being carried by one or two of $SiO_2$ and $ZrO_2$.

Examples of methods for producing a catalyst usable for the above-described dehydration reaction will be described. In the case where the carrier is $SiO_2$, commercially available powdery or spherical $SiO_2$ is usable. Preferably, $SiO_2$ is sized to 100 mesh (0.15 mm) or less so that the active metal is uniformly carried, and is pre-baked at 700° C. for 1 hour in the air in order to remove the moisture. There are various types of $SiO_2$ of various properties. $SiO_2$ having a larger surface area is more preferable because as the surface area is larger, the active metal is dispersed more highly and the generation amount of an aromatic nitrile compound is increased. Specifically, a surface area of 300 $m^2$ or greater is preferable. It should be noted that the surface area of the prepared catalyst may be smaller than the surface area of $SiO_2$ alone as a result of, for example, mutual action of $SiO_2$ and the active metal. In this case, the surface area of the produced catalyst is preferably 150 $m^2$ or greater. The metal oxide acting as an active species may be carried by an impregnation method such as an incipient wetness method, an evaporation-to-dryness method or the like.

A metal salt to be a precursor of a catalyst merely needs to be water-soluble. Examples of usable alkaline metal salts include various compounds such as carbonate, hydrogencarbonate, chloride, nitrate, silicate and the like. An aqueous solution of a precursor formed of a basic metal is impregnated with a carrier, then is dried and baked. The resultant substance is usable as a catalyst. The baking temperature, which depends on the precursor used, is preferably 400 to 600° C.

The amount of the catalyst to be carried may be set appropriately. For example, the amount of the alkaline metal oxide to be carried, converted to the metal, is set to preferably about 0.1 to 1.5 mmol/g, especially preferably about 0.1 to 1 mmol/g, with respect to the total weight of the catalyst. In the case where the amount to be carried is larger than such a value, the activity may be decreased. The amount of the catalyst to be used for the reaction may be set appropriately.

A catalyst preferably usable in the present invention includes a carrier formed of one or two of $SiO_2$ and $ZrO_2$ and one, or at least two, types of alkaline metal oxides carried by the carrier. The catalyst may contain, in addition to the above-described elements, unavoidable impurities incorporated during the production of the catalyst. It is desirable to avoid incorporation of impurities to a maximum possible degree.

The catalyst, usable in the present invention, including a metal oxide acting as an active species carried by the carrier may be in the form of powder or a molded body. In the case of being a molded body, the catalyst may be spherical, pellet-like, cylindrical, ring-shaped, wheel-shaped, granular or the like.

With the method according to the present invention for producing an aromatic nitrile compound using the catalyst, there is no specific limitation on the form of the reaction. A flow reactor such as a batch reactor, a semi-batch reactor, a continuous tank reactor, a tube reactor or the like is usable. For the catalyst, a fixed bed, a slurry bed or the like is usable.

In the production method of the aromatic nitrile compounds according to the present invention, it is desirable to perform the reaction to produce an aromatic nitrile compound while removing by-product water generated by the dehydration reaction. For example, it is desirable to perform reflux or distillation or to provide a dehydration agent such as zeolite or the like in the system, so that the reaction is performed while the by-product water is removed. As a result of the active studies made by the present inventors, it has been found that the production amount of an aromatic nitrile compound is increased as follows by use of a reaction distillation device having a decompression device attached thereto. The catalyst, an aromatic amide compound and diphenylether are put into a reaction tube, the pressure is reduced to control the temperature of the reaction solution, and diphenylether is refluxed to distill the reaction liquid to separate and remove the by-product water from the system.

Diphenylether has a high boiling point of about 259° C., and is preferable for the dehydration reaction.

Desirably, the reaction conditions are selected in accordance with the dehydration reaction speed, the boiling point of diphenylether, generation of pyridine as a by-product as a result of the reaction, and the cost performance.

The usual reaction conditions for the method for producing an aromatic nitrile compound according to the present invention may be as follows. The temperature of the reaction solution is 170 to 230° C.; the pressure is normal pressure (101.3 (kPa) (760 Torr) to reduced pressure (13.3 (kPa) (100 Torr)); and the time is several hours to about 100 hours. The reaction conditions are not limited to the above.

For example, the temperature of the reaction solution is preferably 180 to 228° C., and more preferably 190 to 210° C. The reaction pressure is preferably 1.33 to 60 (kPA) (10 to 450 Torr), and more preferably 13.3 to 53.3 (kPa) (100 to 400 Torr). The reaction time is preferably 4 to 24 hours, and more preferably 8 to 24 hours.

In the case where a molecular sieve is used as the dehydration agent, there is no specific limitation on the type or the shape of the molecular sieve. For example, a general molecular sieve that has a high water absorption rate such as 3A, 4A, 5A or the like and is spherical or pellet-like is usable. For example, Zeolum produced by Tosoh Corporation is usable. Preferably, the molecular sieve is dried in advance, for example, at 300 to 500° C. for about 1 hour.

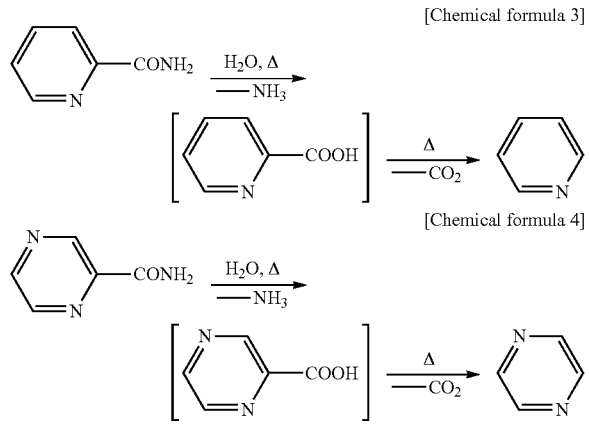

[Chemical formula 3]

[Chemical formula 4]

In the dehydration reaction of an aromatic amide compound, it is considered that as a result of the above-described decomposition of the aromatic amide compound, an aromatic carboxylic acid is generated, from which pyridine or pyrazine is generated as a by-product. However, the reaction solution obtained by the dehydration reaction performed under the reaction conditions according to the present invention contains an unreacted aromatic amide compound, an aromatic nitrile compound as a reaction product, and diphenylether, but does not contain the by-product represented by each of the above formulas at most at all.

The melting points of the substances are as follows: 110° C. (2-picolinamide), 24° C. (2-cyanopyridine), 190° C. (pyrazinamide), 19° C. (cyanopyrazine), and 28° C. (diphenylether). The boiling points of the substances are as follows: 275° C. (2-picolinamide), 215° C. (2-cyanopyridine), 357° C. (pyrazinamide), 87° C./6 mmHg (cyanopyrazine), 100° C. (water), and 259° C. (diphenylether). Therefore, the reaction phases are all liquid except that the catalyst is solid. A reaction distillation device having a decompression device attached thereto is used. A distillation column is heated to have a temperature that is higher than the boiling point of water at the reaction pressure and lower than the boiling point of diphenylether. The reaction solution is heated to a temperature that is higher than, or equal to, the boiling point of diphenylether at the pressure reaction and lower than the boiling point of 2-picolinamide. With such an arrangement, diphenylether partially gasified in the reaction system is cooled by a cooling device and returns to the reaction tube. The by-product water is efficiently separated from the reaction solution by distillation and removed outside the system. Therefore, a nitrile regeneration reaction advances at high speed, and thus the time of the dehydration reaction is significantly shortened.

The boiling point of diphenylether is considered to be higher than the boiling point of an aromatic nitrile compound and the boiling point of water and lower than the boiling point of an aromatic amide compound. Diphenylether fulfilling the relationship between the boiling points between the reaction substances is used, so that the dehydration reaction is performed highly efficiently and the aromatic nitrile compound is recovered easily.

The boiling points of the substances present in the reaction system are different from each other as described above. Therefore, the substances are easily separated by distillation.

<2. Method for Producing a Carbonate Ester Using an Aromatic Nitrile Compound>

As described above, the dehydration reaction of regenerating an aromatic amide compound into an aromatic nitrile compound is performed, and the aromatic amide compound as a target compound is obtained selectively at a high yield with no use of a strong reagent and with the generation of a by-product being suppressed. The reaction speed is significantly improved to significantly shorten the reaction time. Therefore, the speed of regeneration by the dehydration reaction from an aromatic amide compound into an aromatic nitrile compound, and the speed of carbonate ester synthesis from $CO_2$ and an alcohol using the aromatic nitrile compound, are now well balanced so that these reactions can be concurrently adopted. These reactions may be realized as a series of commercial processes. The present inventors applied this knowledge to a method for producing a carbonate ester to conceive the following method for producing a carbonate ester.

(First Reaction Step)

A first reaction step of the method for producing a carbonate ester according to the present invention includes, for example, a reaction of directly reacting an alcohol and carbon dioxide with each other in the presence of a solid catalyst such as $CeO_2$ or the like and an aromatic nitrile compound to generate a carbonate ester (carbonate ester generation reaction).

In this step, an alcohol and carbon dioxide are reacted with each other. As a result, a carbonate ester and also water are generated. The aromatic nitrile compound, which is present in the system, and the generated water are subjected to a hydration reaction to generate an aromatic amide compound. Thus, the water generated by the reaction of the alcohol and carbon dioxide is removed from the reaction system, or is reduced in the amount, so that the generation of the carbonate ester is promoted. For example, the reaction is expressed as follows.

[Chemical formula 5]

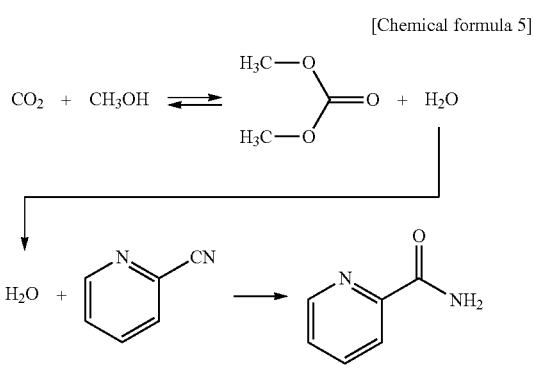

(Alcohol)

As the alcohol, any one, or two or more, selected from primary alcohol, secondary alcohol and tertiary alcohol are usable. Examples of preferable alcohols include methanol, ethanol, 1-propanol, isopropanol, 1-butanol, 1-pentanol, 1-hexanol, 1-heptanol, 1-octanol, 1-nonanol, allylalcohol, 2-methyl-1-propanol, cyclohexanemethanol, benzylalcohol, ethyleneglycol, 1,2-propanediol, and 1,3-propanediol. These alcohols increase the yield of the target product and also increase the reaction speed. The carbonate esters generated by use of the above-listed alcohols are respectively dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diallyl carbonate, di-2-methyl-propyl carbonate, dicyclohexanemethyl carbonate, dibenzyl carbonate, ethylene carbonate, 1,2-propylene carbonate, and 1,3-propylene carbonate.

In the case where the obtained carbonate ester is used as a material of diallyl carbonate, it is preferable to use an alcohol having a carbon number of 1 to 6, and it is more preferable to use an alcohol having a carbon number of 2 to 4.

It is preferable to use a monohydric alcohol or a dihydric alcohol.

(Catalyst Usable for Producing a Carbonate Ester)

In the first reaction step of the method for producing a carbonate ester, it is preferable to use one or both of $CeO_2$ and $ZrO_2$ as a solid catalyst. For example, it is preferable to use only $CeO_2$, only $ZrO_2$, a mixture of $CeO_2$ and $ZrO_2$, a solid solution of $CeO_2$ and $ZrO_2$, or a composite oxide of $CeO_2$ and $ZrO_2$. It is especially preferable to use only $CeO_2$. The mixing ratio of $CeO_2$ and $ZrO_2$ in the solid solution or the composite oxide is basically 50:50, but may be changed optionally.

The catalyst used in the first reaction step may be in the form of powder or a molded body. In the case of being a molded body, the catalyst may be spherical, pellet-like, cylindrical, ring-shaped, wheel-shaped, granular or the like.

(Carbon Dioxide)

In the present invention, carbon dioxide prepared as industrial gas, or carbon dioxide separated and recovered from exhaust gas of plants producing various products, steel manufacturing plants, power plants or the like, is usable.

(Solvent in the Carbonate Ester Generation Reaction)

For the carbonate ester generation reaction, it is preferable to use a solvent having a boiling point higher than that of the amide compound to be produced. More preferably, the solvent in the carbonate ester generation reaction contains at least one of dialkylbenzene, alkylnaphthalene, and diphenylbenzene. Specific examples of preferable solvents include, for example, barrel process oil B-28AN and barrel process oil B-30 (produced by Matsumura Oil Co., Ltd.), each of which a contains component such as dialkylbenzene, alkylnaphthalene, diphenylbenzene or the like.

(Separation by Distillation)

After the reaction, the obtained substance was distilled to be separated into a carbonate ester as a main product, an aromatic amide compound as a by-product, an unreacted aromatic nitrile compound, and a solid catalyst such as $CeO_2$ or the like. Thus, the products are recovered.

(Second Reaction Step)

In a second reaction step according to the present invention, the aromatic amide compound generated as a by-product in the first reaction step is separated from the system after the carbonate ester generation reaction, and an aromatic nitrile compound is produced by a dehydration reaction. The second reaction step corresponds to the above-described method for producing the aromatic nitrile compound, and thus will not be described in detail.

(Reuse of the Aromatic Nitrile Compound)

The aromatic nitrile compound regenerated by the second reaction step is reusable for the first reaction step (hydration reaction).

According to the present invention, as described above, the dehydration reaction of an aromatic amide compound uses diphenylether, which has a boiling point higher than that of the aromatic nitrile compound to be generated and lower than that of the aromatic amide compound as the material, and the temperature of the reaction solution is adjusted. With such an arrangement, the step of solid-liquid separation of the catalyst is made unnecessary, and the aromatic nitrile compound is easily recovered. In the carbonate ester generation reaction, a catalyst having a boiling point higher than that of aromatic carboamide is used, so that the step of solid-liquid separation of the catalyst is made unnecessary. As can be seen, according to the present invention, a series of reactions are advanced while the components are separated from each other only by distillation with no need to perform a step of solid-liquid separation of the catalyst. Thus, an efficient process as described below in detail is realized.

<3. Device for Producing a Carbonate Ester>

Figure 2:
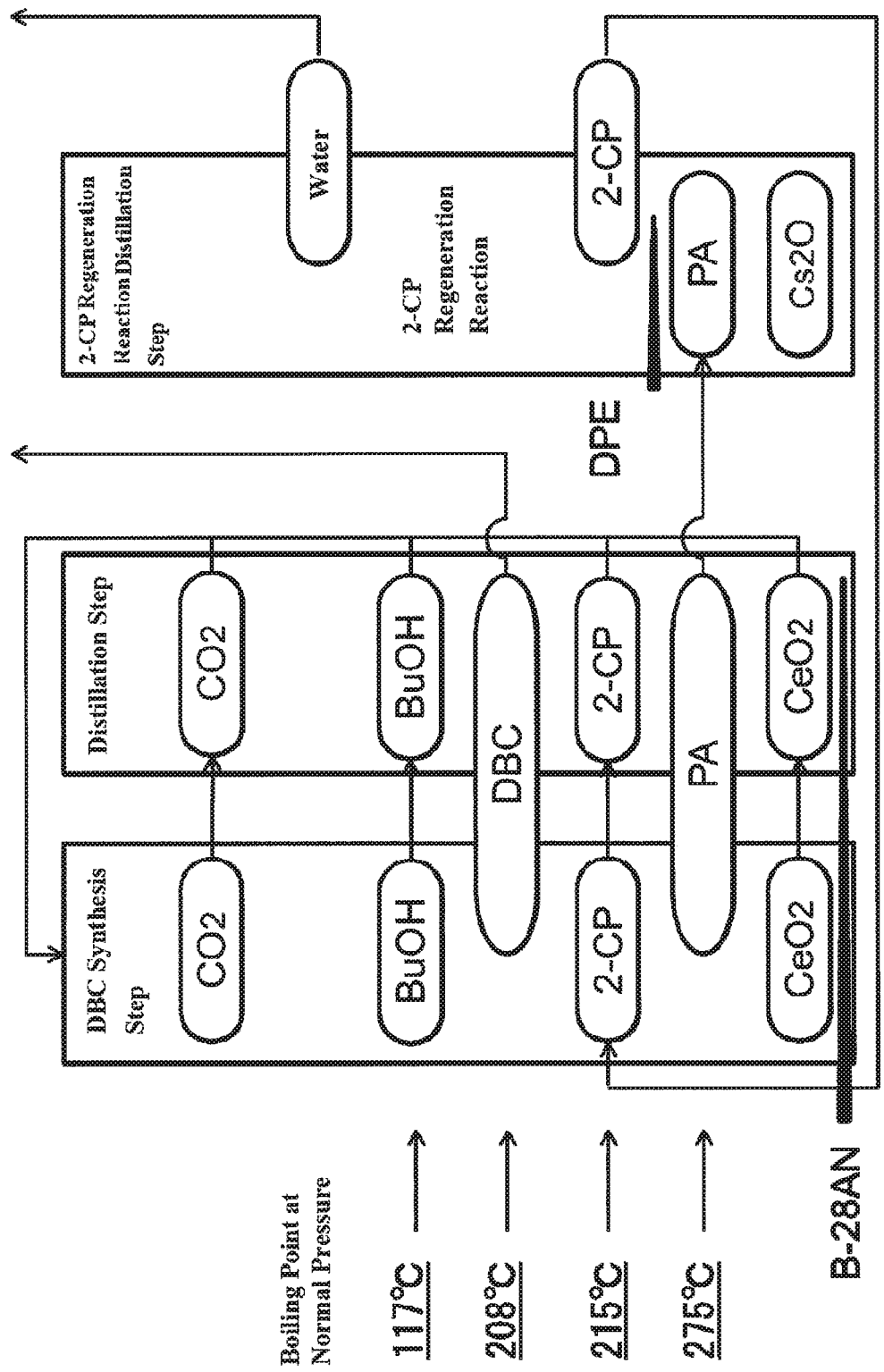
FIG. 2 is a chart showing the state of each of substances at each of steps in the production performed by use of the production device shown in FIG. 1

Now, a production device usable in the present invention will be described in detail by way of a specific example. FIG. 1 shows an example of preferable production device. FIG. 2 schematically shows the state of each of the substances in each of the steps performed by the production device.

(First Reaction Step)

In the first reaction step, a carbonate ester reactor 1 (first reaction portion) is filled with one or both of $CeO_2$ and $ZrO_2$ as a solid catalyst (solid phase), alcohol (1-butanol (BuOH); liquid phase), 2-cyanopyridine (2-CP; liquid), barrel process oil (B-28AN; liquid phase) as a solvent, and carbon dioxide ($CO_2$; gas phase) supplied via a pressure raising blower (not shown). The solid catalyst ($CeO_2$; solid phase) may be newly supplied before the reaction or recovered from a catalyst separation column 2. New 2-cyanopyridine may be used at the start of the reaction. Alternatively, 2-cyanopyridine 22 (liquid phase) regenerated from the unreacted 2-cyanopyridine 19 (gas phase) separated and purified in a dehydration agent separation column 3 and an amide separation column 4 and 2-picolinamide purified in a water separation column 7 is reusable.

In a direct synthesis device for a carbonate ester usable in the present invention, one or both of $CeO_2$ and $ZrO_2$ are used as a solid catalyst. The synthesis device may be a flow reactor such as a batch reactor, a semi-batch reactor, a continuous tank reactor, a tube reactor or the like.

(Temperature of the Reaction Solution)

The temperature of the reaction solution in the carbonate ester reactor 1 is preferably 50 to 300° C. In the case where the temperature of the reaction solution is lower than 50° C., the reaction speed is low, and the carbonate ester synthesis reaction or the hydration reaction with 2-cyanopyridine does not advance almost at all. In this case, the productivity of the carbonate ester tends to be low. In the case where the temperature of the reaction solution is higher than 300° C., the reaction speed of each reaction is high, but the carbonate ester is easily decomposed or denatured and 2-picolinamide is easily reacted with an alcohol. Therefore, the yield of the carbonate ester tends to be low. The temperature of the reaction solution in the carbonate ester reactor 1 is more preferably 100 to 150° C. The preferable temperature is considered to vary in accordance with the type or the amount of the solid catalyst, or the amount or the ratio of the materials (alcohol and 2-cyanopyridine). Thus, it is preferable to set the optimum temperature optionally. Since the preferable temperature of the reaction solution is 100 to 150° C., it is desirable to pre-heat the materials (alcohol and 2-cyanopyridine) with steam or the like on a stage before the carbonate ester reactor 1.

(Reaction Pressure)

The reaction pressure in the carbonate ester reactor 1 is preferably 0.1 to 20 MPa (absolute reaction). In the case where the reaction pressure is lower than 0.1 MPa (absolute reaction), a decompression device is required, which makes the facilities complicated and costly. In addition, a motive power energy to reduce the pressure is necessary, which decreases the energy efficiency. In the case where the reaction pressure is higher than 20 MPa (absolute reaction), the hydration reaction with 2-cyanopyridine does not easily advance, which decreases the yield of the carbonate ester. In addition, a motive power energy to raise the pressure is necessary, which decreases the energy efficiency. From the point of view of increasing the yield of the carbonate ester, the reaction pressure is more preferably 0.5 to 15 MPa (absolute pressure), and still more preferably 1.0 to 10 MPa (absolute pressure).

(Amount of 2-cyanopyridine)

2-cyanopyridine used for the hydration reaction is desirably introduced into the reactor before the reaction in a molar amount that is 0.2 times or greater and 5 times or less of the theoretical molar amount of water generated as a by-product by the reaction of the alcohol and $CO_2$ as the materials. The molar amount of 2-cyanopyridine is more desirably, 0.5 times or greater and 3 times or less, and especially desirably 0.8 times or greater and 1.5 times or less, of the theoretical molar amount of water generated as a by-product by the reaction of the alcohol and $CO_2$ as the materials. In the case where the molar amount of 2-cyanopyridine is too small, the amount of 2-cyanopyridine contributing to the hydration reaction is small, which may decrease the yield of the carbonate ester. By contrast, in the case where the molar amount of 2-cyanopyridine is too large with respect to the alcohol, the by-reaction of 2-cyanopyridine is undesirably increased. The amounts of the alcohol and 2-cyanopyridine with respect to the solid catalyst are considered to vary in accordance with the type or the amount of the solid catalyst, the type or the amount of the alcohol, or the ratio of the alcohol and 2-cyanopyridine. Thus, it is desirable to set the optimum amounts appropriately.

(Separation of the Reaction Products)

The separation of the reaction products is entirely performed by distillation. After the reaction in the carbonate ester reactor 1, a reaction solution 10 is transported to the catalyst separation column 2. From the bottom of the catalyst separation column 2, the catalyst and the solvent (in this example, barrel process oil (B-28AN) (liquid phase; 11)) are recovered. From the top of the catalyst separation column 2, $CO_2$ (12) and a mixture (13) of BuOH, dibutyl carbonate (DBC), 2-cyanopyridine and 2-picolinamide are recovered. The catalyst, the solvent and $CO_2$ that are recovered are recycled to the carbonate ester reactor 1.

The mixture (13) recovered from the catalyst separation column 2 is transported to the dehydration agent separation column 3. From the bottom of the dehydration agent separation column 3, a mixture (14) of 2-cyanopyridine and 2-picolinamide is recovered. From the top of the dehydration agent separation column 3, BuOH and DBC (15) are recovered.

The mixture (14) recovered from the bottom of the dehydration agent separation column 3 is transported to the amide separation column 4. From the bottom of the amide separation column 4, 2-picolinamide (18) is recovered. From the top of the amide separation column 4, 2-cyanopyridine (19) is recovered. The recovered 2-cyanopyridine is recycled to the carbonate ester reactor 1. The 2-picolinamide (18) recovered from the bottom of the amide separation column 4 is transported to a nitrile regeneration reactor 6.

The BuOH and the DBC (15) recovered from the top of the dehydration agent separation column 3 are transported to a carbonate ester recovery column 5. From the bottom of the carbonate ester recovery column 5, DBC (16) is recovered. From the top of the carbonate ester recovery column 5, BuOH (17) is recovered. The recovered BuOH is recycled to the carbonate ester reactor 1.

The 2-picolinamide (2-PA; 18) recovered from the amide separation column 4 is transferred to the nitrile regeneration reactor 6 (second reaction portion) to be regenerated into 2-cyanopyridine.

(Second Reaction Step)

In the second reaction step, 2-cyanopyridine (2-CP) is generated by the dehydration reaction of 2-picolinamide in the nitrile regeneration reactor 6. The production device used in the present invention (nitrile regeneration reactor 6) performs the dehydration reaction of 2-picolinamide in the presence of a catalyst containing a basic metal oxide and diphenylether to generate 2-cyanopyridine. There is no specific limitation on the form of the reaction. A flow reactor such as a batch reactor, a semi-batch reactor, a continuous tank reactor, a tube reactor or the like is usable. For the catalyst, a fixed bed, a slurry bed or the like is usable. The temperature of the nitrile regeneration reactor 6 is variable in accordance with the form of the reaction. A reaction distillation device having a decompression device attached thereto is used. The distillation column is heated to have a temperature that is higher than the boiling point of water at the reaction pressure and lower than the boiling point of diphenylether. The reaction solution is heated to a temperature that is higher than, or equal to, the boiling point of diphenylether at the pressure reaction and lower than the boiling point of 2-picolinamide. With such an arrangement, diphenylether partially gasified in the reaction system is cooled by a cooling device and returns to the reaction tube. The by-product water is efficiently separated from the reaction solution by distillation and removed outside the system. Therefore, the nitrile regeneration reaction advances at high speed.

2-cyanopyridine (22) may be recovered from the water separation column 7 during the reaction or separated by distillation and recovered after the reaction. The recovered 2-cyanopyridine (22) is transported to the carbonate ester reactor 1 and reused for the production of the carbonate ester.

As described above, according to the present invention, a reaction product and a compound to be reused are separated from each other merely by distillation, with no need of solid-liquid separation. Therefore, according to the present invention, a carbonate ester is produced efficiently with a simpler production device and a smaller number of production steps.

Hereinafter, the present invention will be described in more detail by way of examples. The present invention is not limited to any of the following examples. First, examples and comparative examples of method for producing cyanopyridine will be described.

EXAMPLE 1

$SiO_2$ (CARiACT, G-6, surface area: 535 m$^2$/g; produced by Fuji Silysia Chemical Ltd.) as a carrier was sized to 100 mesh or less, and pre-baked at 700° C. for about 1 hour. Then, in order to carry Cs as an alkaline metal, an aqueous solution was prepared using $Cs_2CO_3$ (produced by Wako Pure Chemical Industries, Ltd.) such that the final amount of Cs metal to be carried would be 0.5 mmol/g, and $SiO_2$ was impregnated with the aqueous solution. Then, the resultant substance was dried at 110° C. for about 6 hours and was baked at 500° C. for about 3 hours. As a result, a $Cs_2O/SiO_2$ catalyst was obtained. An $Na_2O/SiO_2$ catalyst was produced by substantially the same method as the $Cs_2O/SiO_2$ catalyst.

Next, a 3-necked round-bottom flask used as a reactor was provided with a magnetic stirrer, the $Cs_2O/SiO_2$ catalyst (1.0 g (Cs: 0.5 mmol)), 2-picolinamide (2-PA; 6.1 g (50 mmol); produced by Tokyo Chemical Industry Co., Ltd.), and diphenylether (212.5 g (1.25 mol); produced by Tokyo Chemical Industry Co., Ltd.).

A thermometer and a first air-cooling tube as a distillation column were attached to the reactor. A distilling head having a thermometer attached thereto was attached to a top end of the first air-cooling tube. A second air-cooling tube, a receiver, and a vacuum pump were connected with the distilling head. The resultant device was to be used as a reaction distillation device. A ribbon heater was wound around the first air-cooling tube, so that the temperature of the first air-cooling tube would be adjustable. A cooling trap was cooled with liquid nitrogen, so that gasified pyridine would be recovered.

Then, the pressure in the reaction distillation device was reduced by the vacuum pump to 13.3 kPa (100 Torr). The first air-cooling tube was heated to 60° C., which was higher than the boiling point of water at the reaction pressure and lower than the boiling point of diphenylether. The reaction solution was maintained in a boiled state at 184° C., which was higher than, or equal to, the boiling point of diphenylether at the reaction pressure and lower than the boiling point of 2-picolinamide. The temperatures were adjusted in this manner, so that the reaction was performed while diphenylether partially gasified in the reaction system was cooled in the first air-cooling tube and returned to the reactor, and the by-product water was separated by distillation and removed outside the system without being returned to the reactor.

The start of the reaction was set to the timing when the reaction solution started to be boiled, and the reaction was continued for 24 hours.

After the reaction, the temperature of the reaction system was cooled to room temperature. The reaction solution was sampled and diluted two-fold with ethanol, and 1-hexanol was added thereto as an internal standard substance. The resultant substance was subjected to a qualitative analysis with GC-MS (gas chromatograph-mass spectrometer) and to a quantitative analysis with FID-GC. As a result, 2-cyanopyridine was generated as shown in Table 1. The yield of 2-cyanopyridine was 35.7 mol %, and the generation ratio of pyridine as a by-product was suppressed to 0.3 mol %.

EXAMPLES 2 THROUGH 5, 7 AND 8

In examples 2 through 5, 7, and 8, 2-cyanopyridine was produced from 2-picolinamide under the conditions in which at least one of the concentration of 2-picolinamide in the reaction solution, the type of the catalyst, the type of the additive to the reaction solution, the temperature of the reaction solution, the reaction pressure, the temperature of the first air-cooling tube and the reaction time was different from that in example 1 (see Table 1). The yield of 2-cyanopyridine and the generation ratio of pyridine as a by-product were as shown in Table 1.

EXAMPLE 6

In example 6, pyrazinamide (produced by Sigma-Aldrich) was used instead of 2-picolinamide. Cyanopyrazine was produced from pyrazinamide under the conditions in which the temperature of the reaction solution, the reaction pressure, the temperature of the first air-cooling tube and the reaction time were different from those in example 1 (see Table 1). The yield of cyanopyrazine and the generation ratio of pyrazine as a by-product were as shown in Table 1.

COMPARATIVE EXAMPLES 1 THROUGH 17

In comparative examples 1 through 6, 2-cyanopyridine was produced from 2-picolinamide, or cyanopyrazine was produced from pyrazinamide, under the conditions in which at least one of the type of the additive to the reaction solution, the temperature of the reaction solution, the reaction pressure, the temperature of the first air-cooling tube, the reaction time and the method of dehydration was different from that in examples 1 through 8 (see Table 1). In the comparative examples except for comparative example 4, a Soxhlet extractor filled with molecular sieve 4A (dried in advance at 300° C. for 1 hour) and a Liebig condenser were connected with a reaction tube, and the resultant device was used as the reaction device. The temperature of the condenser was set to 10° C., and the magnetic stirrer was set to stir at 600 rpm. The reaction was performed after the condenser, the Soxhlet extractor and the test tube were purged with Ar gas. The yield of 2-cyanopyridine or the like and the generation ratio of pyridine or the like as a by-product were as shown in Table 1.

Table 1 shows the results of examples 1 through 8 and comparative examples 1 through 17.

TABLE 1

| Example/Comparative Example | Substrate | Substrate amount mmol | Catalyst type | Catalyst amount mol % | Additive to reaction solution | Additive boiling point ° C. | Additive amount Molar ratio | Reaction solution temperature ° C. | Reaction solution state |
|---|---|---|---|---|---|---|---|---|---|
| Example 1 | 2-PA | 50 | Cs2O/SiO2 | 1.0 | Diphenylether | 259 | 25 | 184 | Boiled |
| Example 2 | 2-PA | 5 | Cs2O/SiO2 | 1.0 | Diphenylether | 259 | 25 | 229 | Boiled |
| Example 3 | 2-PA | 50 | Cs2O/SiO2 | 1.0 | Diphenylether | 259 | 25 | 229 | Boiled |
| Example 4 | 2-PA | 5 | Na2O/SiO2 | 1.0 | Diphenylether | 259 | 25 | 229 | Boiled |
| Example 5 | 2-PA | 5 | Na2O/SiO2 | 1.0 | Diphenylether 2-cyanopyridine | 259 | 25, 2 | 229 | Boiled |
| Example 6 | Pyradine amide | 50 | Cs2O/SiO2 | 1.0 | Diphenylether | 259 | 25 | 228 | Boiled |
| Example 7 | 2-PA | 5 | Cs2O/SiO2 | 1.0 | Diphenylether | 259 | 25 | 166 | Boiled |
| Example 8 | 2-PA | 5 | Cs2O/SiO2 | 1.0 | Diphenylether | 259 | 25 | 259 | Boiled |
| Comparative example 1 | 2-PA | 5 | Na2O/SiO2 | 1.0 | Mesitylene | 165 | 25 | 165 | Boiled |
| Comparative example 2 | 2-PA | 5 | Na2O/SiO2 | 1.0 | Mesitylene | 165 | 25 | 165 | Boiled |
| Comparative example 3 | Pyradine amide | 15 | Cs2O/SiO2 | 1.0 | Mesitylene | 165 | 25 | 165 | Boiled |
| Comparative example 4 | 2-PA | 15 | Na2O/SiO2 | 1.0 | 3,4-Dimethoxytoluene | 218 | 25 | 223 | Boiled |
| Comparative example 5 | 2-PA | 15 | Cs2O/SiO2 | 1.0 | 1-tert-Butyl-3,5-dimethylbenzene | 202 | 25 | 204 | Boiled |
| Comparative example 6 | 2-PA | 15 | Cs2O/SiO2 | 1.0 | Cyclohexylbenzene | 236 | 25 | 202 | Not boiled |
| Comparative example 7 | 2-PA | 15 | Cs2O/SiO2 | 1.0 | 3,5-Dimethylanisole | 193 | 25 | 195 | Boiled |
| Comparative example 8 | 2-PA | 15 | Na2O/SiO2 | 1.0 | 3-Methylanisole | 177 | 25 | 180 | Boiled |
| Comparative example 9 | 2-PA | 15 | Cs2O/SiO2 | 1.0 | 4-tert-Butylanisole | 222 | 25 | 202 | Not boiled |
| Comparative example 10 | 2-PA | 50 | Cs2O/SiO2 | 1.0 | Diphenyl Sulfide | 296 | 25 | 182 | Boiled |
| Comparative example 11 | 2-PA | 15 | Cs2O/SiO2 | 1.0 | Diphenyl Sulfide | 296 | 25 | 202 | Not boiled |
| Comparative example 12 | 2-PA | 7.5 | Na2O/SiO2 | 1.0 | Amylbenzene | 205 | 25 | 207 | Boiled |
| Comparative example 13 | 2-PA | 15 | Cs2O/SiO2 | 1.0 | 1-Methylnaphthalene | 241 | 25 | 203 | Not boiled |
| Comparative example 14 | 2-PA | 15 | Cs2O/SiO2 | 1.0 | 1-Methoxynaphthalene | 271 | 25 | 202 | Not boiled |
| Comparative example 15 | 2-PA | 15 | Cs2O/SiO2 | 1.0 | Diamyl Ether | 186 | 25 | 189 | Boiled |
| Comparative example 16 | 2-PA | 15 | Cs2O/SiO2 | 1.0 | Dibenzyl Ether | 298 | 25 | 201 | Not boiled |
| Comparative example 17 | 2-PA | 15 | Cs2O/SiO2 | 1.0 | Diethylene Glycol Diethyl Ether | 188 | 25 | 191 | Boiled |

| Example/Comparative Example | Reaction pressure kPa | Reaction pressure Torr | 1st air-cooling tube temperature ° C. | Reaction time h | Dehydration method | Nitrile yield mol % | Pyridine generation ratio (*1) mol % | Nitrile/pyridine (*2) mol %/mol % |
|---|---|---|---|---|---|---|---|---|
| Example 1 | 13.3 | 100 | 60 | 24 | Disllation and removal at reduced pressure | 35.7 | 0.3 | 108 |
| Example 2 | 53.3 | 400 | 95 | 8 | Disllation and removal at reduced pressure | 74.7 | 3.4 | 22 |
| Example 3 | 54.3 | 400 | 90 | 4 | Disllation and removal at reduced pressure | 48.4 | 2.0 | 24 |
| Example 4 | 55.3 | 400 | 95 | 8 | Disllation and removal at reduced pressure | 58.3 | 1.8 | 33 |
| Example 5 | 59.1 | 443 | 95 | 24 | Disllation and removal at reduced pressure | 75.4 | 2.1 | 36 |
| Example 6 | 55.3 | 400 | 90 | 4 | Disllation and removal at reduced pressure | 39.7 | 1.3 | 30 |
| Example 7 | 6.67 | 50 | 45 | 24 | Disllation and removal at reduced pressure | 18.7 | Less than detection limit | |
| Example 8 | 101.3 | 760 | — | 4 | Molecular sieve | 74.9 | 6.5 | 12 |
| Comparative example 1 | 101.3 | 760 | — | 400 | Molecular sieve | 79.2 | 0.3 | 232 |
| Comparative example 2 | 101.3 | 760 | — | 24 | Molecular sieve | 9.9 | Less than detection limit | — |
| Comparative example 3 | 101.3 | 760 | — | 24 | Molecular sieve | 2.70 | Less than detection limit | — |
| Comparative example 4 | 101.3 | 760 | — | 24 | Molecular sieve | 13.3 | 1.9 | 7 |

TABLE 1-continued

| | | | | | | | | |
|---|---|---|---|---|---|---|---|---|
| Comparative example 5 | 101.3 | 760 | — | 24 | Molecular sieve | 20.0 | 3.6 | 6 |
| Comparative example 6 | 101.3 | 760 | — | 24 | Molecular sieve | 4.82 | 1.5 | 3 |
| Comparative example 7 | 101.3 | 760 | — | 24 | Molecular sieve | 0.49 | 0.1 | 4 |
| Comparative example 8 | 101.3 | 760 | — | 24 | Molecular sieve | 2.54 | Less than detection limit | |
| Comparative example 9 | 101.3 | 760 | — | 24 | Molecular sieve | 16.0 | 0.5 | 32 |
| Comparative example 10 | 6.13 | 46 | 45 | 12 | Disllation and removal at reduced pressure | 18.3 | 0.3 | 53 |
| Comparative example 11 | 101.3 | 760 | — | 24 | Molecular sieve | 17.4 | 1.28 | 14 |
| Comparative example 12 | 101.3 | 760 | — | 24 | Molecular sieve | Reaction solution blackened with by-product | | |
| Comparative example 13 | 101.3 | 760 | — | 24 | Molecular sieve | Reaction solution blackened with by-product | | |
| Comparative example 14 | 101.3 | 760 | — | 24 | Molecular sieve | Reaction solution blackened with by-product | | |
| Comparative example 15 | 101.3 | 760 | — | 24 | Molecular sieve | Reaction solution blackened with by-product | | |
| Comparative example 16 | 101.3 | 760 | — | 24 | Molecular sieve | Reaction solution blackened with by-product | | |
| Comparative example 17 | 101.3 | 760 | — | 24 | Molecular sieve | Reaction solution blackened with by-product | | |

(*1) Pyrazine generation ratio (mol %) in example 6 and comparative example 3
(*2) Nitrile/pyrazine generation ratio (mol %/mol %) in example 6 and comparative example 3

As described above, the dehydration reaction in examples 1 through 8 using diphenylether as an additive to the reaction solution resulted in generating the aromatic nitrile compound as a target compound at a high yield while suppressing the generation of pyridine and so on as by-products. Especially in examples 1 through 6, in which the temperature of the reaction solution was adjusted to the range of 170 to 230° C., a high yield of the nitrile compound and the reduction of the generation of the by-product were both confirmed be realized.

Figure 3:
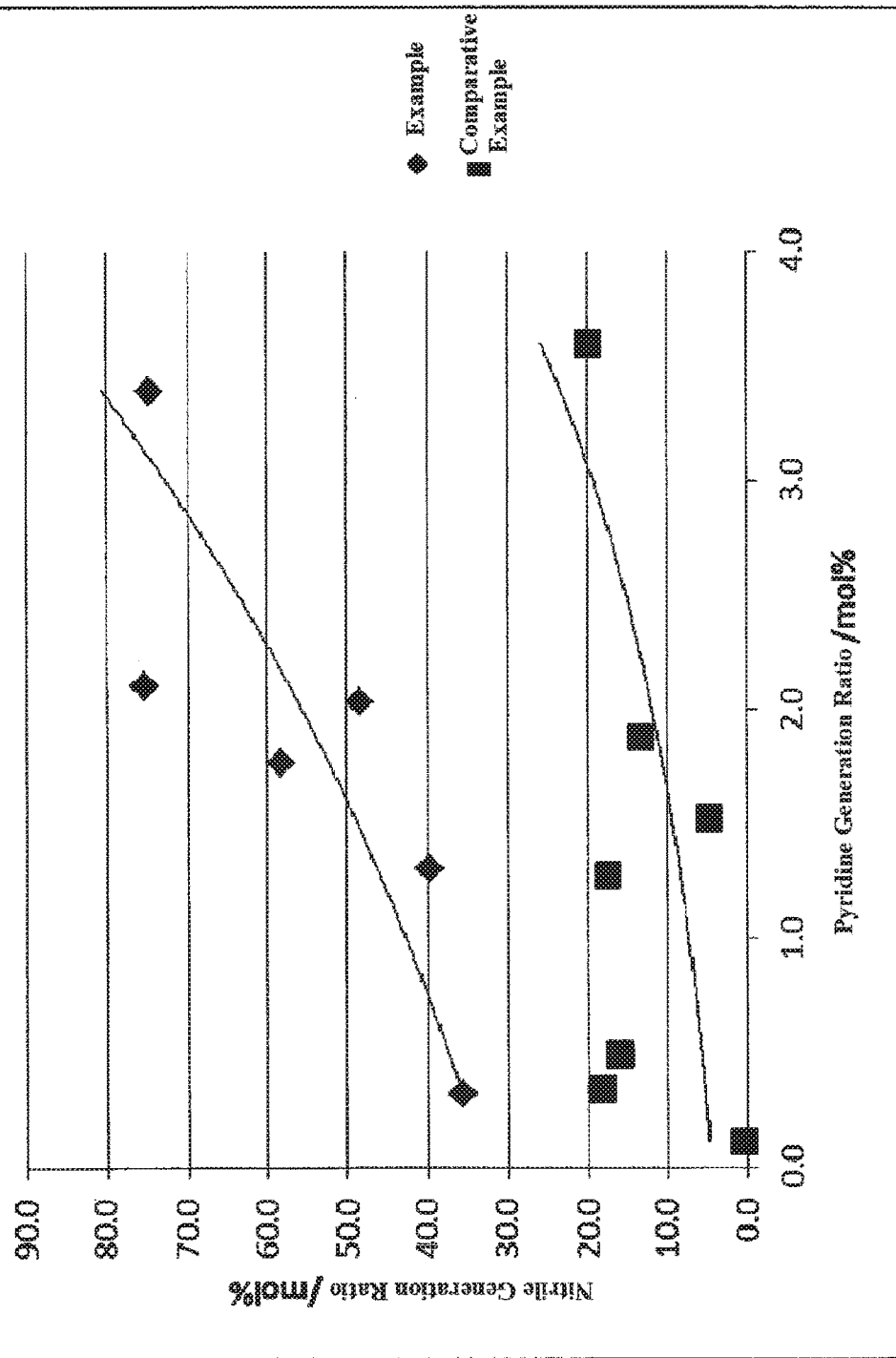
FIG. 3 is a graph showing the ratio of the yields (generation ratios) of nitrile and pyridine in an example and a comparative example.

By contrast, the comparative examples, in which diphenylether was not used and the reaction conditions were different from those in the examples, resulted in a low yield of the aromatic nitrile compound (see FIG. 3, which shows the results of an example and a comparative example exhibiting a relatively high yield). In some of the comparative examples, the generation of pyridine was suppressed, but even in these comparative examples, the yield of the nitrile compound was low. In comparative example 1, the yield of the nitrile compound was high, but the required reaction time was too long and thus comparative example 1 was inferior to the examples.

For evaluation of the catalysts, a control test was performed in which only the type of the catalyst usable in the dehydration reaction was changed. In the control test, the type of the additive to the reaction solution was different from that in example 1 or the like. The test was performed under the reaction conditions in accordance with the boiling point of the additive to the reaction solution. The results are shown in Table 2.

TABLE 2

| Example/ Comparative Example | Substrate | Substrate amount mmol | Catalyst type | Catalyst amount mol % | Additive to reaction solution | Additive boiling point ° C. | Additive amount Molar ratio | Reaction solution temperature ° C. |
|---|---|---|---|---|---|---|---|---|
| Reference example 1 | 2-PA | 5 | Li2O/SiO2 | 1.0 | Mesitylene | 165 | 25 | 165 |
| Reference example 2 | 2-PA | 5 | Na2O/SiO2 | 1.0 | Mesitylene | 165 | 25 | 165 |
| Reference example 3 | 2-PA | 5 | K2O/SiO2 | 1.0 | Mesitylene | 165 | 25 | 165 |
| Reference example 4 | 2-PA | 5 | Rb2O/SiO2 | 1.0 | Mesitylene | 165 | 25 | 165 |
| Reference example 5 | 2-PA | 5 | Cs2O/SiO2 | 1.0 | Mesitylene | 165 | 25 | 165 |
| Reference example 6 | 2-PA | 5 | CaO/SiO2 | 1.0 | Mesitylene | 165 | 25 | 165 |
| Reference example 7 | 2-PA | 5 | CeO2 | 1.0 | Mesitylene | 165 | 25 | 165 |
| Reference example 8 | 2-PA | 5 | MoO3/SiO2 | 1.0 | Mesitylene | 165 | 25 | 165 |

TABLE 2-continued

| Example/ Comparative Example | Reaction solution state | Reaction pressure kPa | Reaction pressure Torr | Reaction time h | Dehydration method | Nitrile yield mol % | Pydirine generation ratio mol % |
|---|---|---|---|---|---|---|---|
| Reference example 1 | Boiled | 101.3 | 760 | 24 | Molecular sieve | 2.91 | Less than detection limit |
| Reference example 2 | Boiled | 101.3 | 760 | 24 | Molecular sieve | 9.9 | Less than detection limit |
| Reference example 3 | Boiled | 101.3 | 760 | 24 | Molecular sieve | 16.0 | Less than detection limit |
| Reference example 4 | Boiled | 101.3 | 760 | 24 | Molecular sieve | 17.8 | Less than detection limit |
| Reference example 5 | Boiled | 101.3 | 760 | 24 | Molecular sieve | 18.2 | Less than detection limit |
| Reference example 6 | Boiled | 101.3 | 760 | 24 | Molecular sieve | 1.17 | Less than detection limit |
| Reference example 7 | Boiled | 101.3 | 760 | 24 | Molecular sieve | 11.0 | Many peaks of by-product |
| Reference example 8 | Boiled | 101.3 | 760 | 24 | Molecular sieve | 1.54 | Less than detection limit |

As seen from Table 2, in the case where especially $Cs_2O$, $Rb_2O$, $K_2O$ or $Na_2O$ was used as the catalyst for the dehydration reaction according to the present invention, the aromatic nitrile compound was confirmed to be obtained selectively at a high yield.

EXAMPLE 9

A 3-necked round-bottom flask used as a reactor was provided with a magnetic stirrer, the $Cs_2O/SiO_2$ catalyst (10 g (Cs: 5 mmol)), 2-picolinamide (61 g (0.5 mol); produced by Tokyo Chemical Industry Co., Ltd.), and diphenylether (2125 g (12.5 mol); produced by Tokyo Chemical Industry Co., Ltd.). The reaction distillation device was structured in substantially the same manner as in example 1.

The reaction was performed under the same conditions as in example 2 to obtain a reaction solution containing 38.5 g of 2-cyanopyridine.

The reaction distillation device was used to distill the reaction solution at a pressure of 1.3 kPa to obtain 33.5 g of 2-cyanopyridine. As a result of an analysis performed with FID-GC, the purity thereof was 99.9%.

It has been confirmed that in the case where, as described above, diphenylether having a boiling point higher than that of the aromatic nitrile compound to be generated and lower than that of the aromatic amide compound as the material is used and the temperature of the reaction solution is adjusted by pressure control, the reaction speed is significantly improved to shorten the reaction time, the target compound is obtained selectively at a high yield, and the aromatic nitrile compound is recovered easily.

EXAMPLE 20

Now, examples of methods for producing a carbonate ester using cyanopyridine (carbonate ester generation reaction) will be described. The 2-cyanopyridine obtained in example 9 was used. First, $CeO_2$ (HSA20; produced by Solvay) was baked at 600° C. for 3 hours in an air atmosphere to obtain a powdery solid catalyst. A 190 ml autoclave (reactor) was provided with a magnetic stirrer, the solid catalyst (0.17 g (1 mmol)), butanol (7.4 g (100 mmol); produced by Wako Pure Chemical Industries, Ltd.), barrel process oil B-28AN (5 g) as the solvent, and 2-cyanopyridine (5.2 g (50 mmol)). The air in the autoclave was purged three times with $CO_2$, and then $CO_2$ was introduced into the autoclave such that the pressure would be 5 MPa. The temperature of the autoclave was raised to 132° C. with a band heater while a hot stirrer was used for stirring. The timing when the temperature reached the target temperature was set as the reaction start time. During the reaction, the pressure reached 8 MPa. The temperature of the reaction solution was raised to 132° C. as described above, and the reaction was continued for 24 hours. Then, the autoclave was cooled with water. When the autoclave was cooled to room temperature, the pressure in the autoclave was reduced. The solution in the autoclave was diluted two-fold with acetone, and 1-hexanol was added thereto as an internal standard substance. The resultant substance was analyzed with FID-GC. Dibutyl carbonate was obtained in this manner

EXAMPLES 21 THROUGH 53

In examples 21 through 53, a carbonate ester was obtained from an alcohol and $CO_2$ using 2-cyanopyridine under the conditions in which at least one of presence/absence of the solvent, the type of the solvent, the amount of the solvent, the reaction time, the type and the concentration of the alcohol (substrate), and the type and the amount of the catalyst was different from that in example 20. Specifically, the conditions different from those in example 20 were the type and the amount of the solvent in examples 21 through 24 and 47, the reaction time in examples 25 through 28, the value of the alcohol/2-cyanopyridine as the materials in examples 29 through 32 and 48, the amount of the catalyst in examples 33 through 36, the type of the catalyst in examples 37 through 40, the temperature of the reaction solution in examples 41 through 46, the reaction pressure in examples 49 and 50, and the type and the amount of the alcohol as the material in examples 41 through 53.

Table 3 shows the results of the examples of production of the carbonate ester.

TABLE 3

| | Solvent | Substrate | Substrate amount [mmol] | 2-CP amount [mmol] | Nitrile/theoretically generated water Molar amount | Catalyst type | Catalyst amount [mmol] | Reaction solution temperature [° C.] | Reaction pressure [MPa] | Reaction time [h] | Picolinic acid ester amount as by-product mol % | Pyridineimidic acid ester amount as by-product mol % | Carbanic acid ester amount as by-product mol % | Dialkyl carbonate yield mol % |
|---|---|---|---|---|---|---|---|---|---|---|---|---|---|---|
| Example 20 | Barrel process oil as high-boiling point solvent (B-28AN, 5 g used) | BuOH | 100 | 50 | 1.0 | CeO2 (HSA-20) 600° C. 3 h baked | 1.0 | 132 | 8 | 24 | 2.4 | 0.34 | Less than detection limit | 53.0 |
| Example 21 | Barrel process oil as high-boiling point solvent (B-28AN, 15 g used) | BuOH | 100 | 50 | 1.0 | CeO2 (HSA-20) 600° C. 3 h baked | 1.0 | 132 | 8 | 24 | 1.1 | 0.22 | Less than detection limit | 40.1 |
| Example 22 | Barrel process oil as high-boiling point solvent (B-30, 5 g used) | BuOH | 100 | 50 | 1.0 | CeO2 (HSA-20) 600° C. 3 h baked | 1.0 | 132 | 8 | 24 | 1.8 | 0.30 | Less than detection limit | 56.2 |
| Example 23 | Barrel process oil as high-boiling point solvent (B-30, 15 g used) | BuOH | 100 | 50 | 1.0 | CeO2 (HSA-20) 600° C. 3 h baked | 1.0 | 132 | 8 | 24 | 1.2 | 0.23 | Less than detection limit | 44.4 |
| Example 24 | Barrel process oil as high-boiling point solvent (B-30, 5 g used) | BuOH | 100 | 50 | 1.0 | CeO2 (HSA-20) 600° C. 3 h baked | 1.0 | 132 | 8 | 4 | 0.21 | 0.15 | Less than detection limit | 37.7 |
| Example 25 | — | BuOH | 100 | 50 | 1.0 | CeO2 (HSA-20) 600° C. 3 h baked | 1.0 | 132 | 8 | 4 | 0.34 | 0.14 | Less than detection limit | 45.3 |
| Example 26 | — | BuOH | 100 | 50 | 1.0 | CeO2 (HSA-20) 600° C. 3 h baked | 1.0 | 132 | 8 | 12 | 0.92 | 0.28 | Less than detection limit | 55.2 |
| Example 27 | — | BuOH | 100 | 50 | 1.0 | CeO2 (HSA-20) 600° C. 3 h baked | 1.0 | 132 | 8 | 16 | 1.1 | 0.36 | Less than detection limit | 57.4 |
| Example 28 | — | BuOH | 100 | 50 | 1.0 | CeO2 (HSA-20) 600° C. 3 h baked | 1.0 | 132 | 8 | 24 | 1.9 | 0.44 | Less than detection limit | 63.2 |
| Example 29 | — | BuOH | 20 | 100 | 10 | CeO2 (HSA-20) 600° C. 3 h baked | 0.20 | 132 | 8 | 16 | 0.20 | 0.41 | Less than detection limit | 24.1 |
| Example 30 | — | BuOH | 100 | 100 | 2.0 | CeO2 (HSA-20) 600° C. 3 h baked | 1.0 | 132 | 8 | 16 | 1.3 | 0.62 | Less than detection limit | 65.7 |
| Example 31 | — | BuOH | 200 | 50 | 0.50 | CeO2 (HSA-20) 600° C. 3 h baked | 1.0 | 132 | 8 | 16 | 1.7 | 0.15 | Less than detection limit | 44.5 |
| Example 32 | — | BuOH | 300 | 50 | 0.33 | CeO2 (HSA-20) 600° C. 3 h baked | 1.0 | 132 | 8 | 16 | 4.0 | 0.16 | Less than detection limit | 31.8 |
| Example 33 | — | BuOH | 20 | 100 | 10 | CeO2 (HSA-20) 600° C. 3 h baked | 1.0 | 132 | 8 | 4 | 0.84 | 0.56 | Less than detection limit | 59.2 |
| Example 34 | — | BuOH | 20 | 100 | 10 | CeO2 (HSA-20) 600° C. 3 h baked | 2.0 | 132 | 8 | 4 | 2.3 | 1.0 | Less than detection limit | 72.8 |
| Example 35 | — | BuOH | 100 | 50 | 1.0 | CeO2 (HSA-20) 600° C. 3 h baked | 4.0 | 132 | 8 | 4 | 0.43 | 0.13 | Less than detection limit | 49.7 |
| Example 36 | — | BuOH | 100 | 50 | 1.0 | CeO2 (HSA-20) 600° C. 3 h baked | 3.0 | 132 | 8 | 4 | 0.62 | 0.14 | Less than detection limit | 52.9 |

TABLE 3-continued

| | Solvent | Substrate | Substrate amount [mmol] | 2-CP amount [mmol] | Nitrile/theoretically generated water Molar amount | Catalyst type | Catalyst amount [mmol] | Reaction solution temperature [° C.] | Reaction pressure [MPa] | Reaction time [h] | Picolinic acid ester amount as by-product mol % | Pyridineimidic acid ester amount as by-product mol % | Carbanic acid ester amount as by-product mol % | Dialkyl carbonate yield mol % |
|---|---|---|---|---|---|---|---|---|---|---|---|---|---|---|
| Example 37 | — | BuOH | 100 | 50 | 1.0 | CeO2 (HSA-5) unbaked | 1.0 | 132 | 8 | 24 | 1.9 | 3.1 | Less than detection limit | 32.7 |
| Example 38 | — | BuOH | 100 | 50 | 1.0 | CeO2 (HSA-5) 600° C. 3 h baked | 1.0 | 132 | 8 | 24 | 2.0 | 0.40 | Less than detection limit | 66.1 |
| Example 39 | — | BuOH | 100 | 50 | 1.0 | CeO2 (HSA-5) 600° C. 3 h baked | 1.0 | 132 | 8 | 4 | 0.29 | 0.15 | Less than detection limit | 42.6 |
| Example 40 | — | BuOH | 100 | 50 | 1.0 | CeO2 (Daiichi Kigenso) 600° C. 3 h baked | 1.0 | 132 | 8 | 4 | 0.18 | 0.15 | Less than detection limit | 35.4 |
| Example 41 | — | EtOH | 20 | 100 | 10 | CeO2 (HSA-20) 600° C. 3 h baked | 2.0 | 132 | 8 | 4 | 1.5 | 0.71 | 1.1 | 68.2 |
| Example 42 | — | EtOH | 100 | 50 | 1.0 | CeO2 (HSA-20) 600° C. 3 h baked | 1.0 | 132 | 8 | 4 | 0.49 | 0.12 | 0.40 | 56.8 |
| Example 43 | — | EtOH | 20 | 100 | 10 | CeO2 (HSA-20) 600° C. 3 h baked | 2.0 | 120 | 8 | 4 | 0.58 | 0.31 | 0.47 | 64.9 |
| Example 44 | — | EtOH | 100 | 50 | 1.0 | CeO2 (HSA-20) 600° C. 3 h baked | 1.0 | 120 | 8 | 4 | 0.09 | 0.04 | 0.079 | 44.3 |
| Example 45 | — | EtOH | 100 | 50 | 1.0 | CeO2 (HSA-20) 600° C. 3 h baked | 1.0 | 110 | 8 | 4 | 0.03 | 0.02 | Less than detection limit | 33.3 |
| Example 46 | — | EtOH | 100 | 50 | 1.0 | CeO2 (HSA-20) 600° C. 3 h baked | 1.0 | 110 | 8 | 24 | 0.43 | 0.15 | 0.39 | 57.1 |
| Example 47 | Barrel process oil as high-boiling point solvent (B-30, 5 g used) | EtOH | 100 | 50 | 1.0 | CeO2 (HSA-20) 600° C. 3 h baked | 1.0 | 110 | 8 | 24 | 0.29 | 0.48 | 2.1 | 64.2 |
| Example 48 | — | EtOH | 100 | 150 | 3.0 | CeO2 (HSA-20) 600° C. 3 h baked | 1.0 | 110 | 8 | 24 | 0.44 | 0.21 | 0.39 | 62.3 |
| Example 49 | — | EtOH | 100 | 50 | 1.0 | CeO2 (HSA-20) 600° C. 3 h baked | 1.0 | 110 | 1 | 4 | 0.12 | 0.12 | 0.12 | 38.6 |
| Example 50 | — | EtOH | 100 | 50 | 1.0 | CeO2 (HSA-20) 600° C. 3 h baked | 1.0 | 110 | 1 | 24 | 1.9 | 1.6 | 1.7 | 57.5 |
| Example 51 | Barrel process oil as high-boiling point solvent (B-30, 5 g used) | Ethyleneglycol | 50 | 50 | 1.0 | CeO2 (HSA-20) 600° C. 3 h baked | 2.0 | 130 | 8 | 1 | 0.45 | 0.20 | Less than detection limit | 99.0 |
| Example 52 | Barrel process oil as high-boiling point solvent (B-30, 5 g used) | 1,2-propanediol | 50 | 50 | 1.0 | CeO2 (HSA-20) 600° C. 3 h baked | 2.0 | 140 | 8 | 1 | 0.40 | 0.22 | Less than detection limit | 99.0 |
| Example 53 | Barrel process oil as high-boiling point solvent (B-30, 5 g used) | 1,3-propanediol | 50 | 50 | 1.0 | CeO2 (HSA-20) 600° C. 3 h baked | 2.0 | 140 | 8 | 1 | 0.45 | 0.20 | Less than detection limit | 99.0 |

As described above, in examples 20 through 53, the carbonate ester was confirmed to be obtained at a high yield within a short reaction time of 24 hours or shorter while the hydration reaction of the by-product water with an aromatic cyano compound was advanced at the same time with the carbonate ester generation reaction.

EXAMPLE 54

Now, an example of recovery of the catalyst from the carbonate ester reaction solution will be described. A carbonate ester was produced by use of the production device shown in FIG. 1. First, $CeO_2$ (impurity concentration: 0.02% or less; produced by Daiichi Kigenso Kagaku Kogyo Co., Ltd.) was baked at 600° C. for 3 hours in an air atmosphere to obtain a powdery solid catalyst. A 1.9 L autoclave (reactor) with a stirrer was provided with the solid catalyst (1.72 g (10 mmol)), butanol (74.1 g (1 mol); produced by Wako Pure Chemical Industries, Ltd.), barrel process oil B-28AN (50 g) as the solvent, and 2-cyanopyridine (52.1 g (0.5 mol)). The air in the autoclave was purged three times with $CO_2$, and then $CO_2$ was introduced into the autoclave such that the pressure would be 5 MPa. The temperature of the autoclave was raised to 132° C. with a ceramic heater while the substances in the autoclave were stirred. The timing when the temperature reached the target temperature was set as the reaction start time. During the reaction, the pressure reached 8 MPa.

The temperature of the reaction solution was raised to 132° C. as described above, and the reaction was continued for 24 hours. Then, the pressure in the autoclave was returned to the atmospheric pressure. The reaction solution was introduced to a middle portion of a distillation column having a reduced pressure of 2.7 kPa, and simple distillation was performed. From the top of the distillation column, a mixture of BuOH, dibutyl carbonate, 2-cyanopyridine and 2-picolinamide was recovered. From the bottom of the distillation column, the catalyst and barrel process oil were recovered.

A 1.9 L autoclave (reactor) with a stirrer was provided with the catalyst and the solvent recovered above, butanol (74.1 g (1 mol); produced by Wako Pure Chemical Industries, Ltd.), and 2-cyanopyridine (52.1 g (0.5 mol)). The air in the autoclave was purged three times with $CO_2$, and then $CO_2$ was introduced into the autoclave such that the pressure would be 5 MPa. The temperature of the autoclave was raised to 132° C. with a ceramic heater while the substances in the autoclave were stirred. The timing when the temperature reached the target temperature was set as the reaction start time. During the reaction, the pressure reached 8 MPa. After the reaction was continued for 24 hours, the autoclave was cooled with water. When the autoclave was cooled to room temperature, the pressure in the autoclave was reduced and a part of the reaction solution was sampled. The sampled reaction solution was diluted two-fold with acetone, and 1-hexanol was added thereto as an internal standard substance. The resultant substance was analyzed with FID-GC. The yield of dibutyl carbonate was 54 mol %.

The reaction solution was distilled in the order shown in FIG. 1 to obtain 40 g of dibutyl carbonate. An analysis with FID-GC showed that the purity was 99.9%.

The carbonate ester was confirmed to be obtained at a high yield by the carbonate ester generation reaction performed using the catalyst used and recovered.

As described above, it has been confirmed that even in the carbonate ester generation reaction, in the case where a solvent having a boiling point higher than that of aromatic carboamide is used, the components are separated from each other merely by distillation with no need of the step of solid-liquid separation of the catalyst. Thus, an efficient process is realized.

Preferable embodiments of the present invention have been described above in detail with respect to the attached drawings. The present invention is not limited to any of the embodiments. A person of ordinary skill in the art of the present invention would obviously conceive any altered or modified example in the technological scope defined by the claims, and such an altered or modified example is duly encompassed in the technological scope of the present invention.

REFERENCE SIGNS LIST

1 Carbonate ester reactor
2 Catalyst separation column
3 Dehydration agent separation column
4. Amide separation column
5 Carbonate ester recovery column
6 Nitrile regeneration reactor
7 Water separation column
8 Decompression pump

The invention claimed is:

1. A method for producing an aromatic nitrile compound, comprising:
   a dehydration reaction of dehydrating an aromatic amide compound;
   wherein the dehydration reaction is performed in the presence of diphenylether.

2. The method for producing an aromatic nitrile compound according to claim 1, wherein the dehydration reaction is performed in the presence of boiling diphenylether.

3. The method for producing an aromatic nitrile compound according to claim 2, wherein the diphenylether has a boiling point that is higher than the boiling point of the aromatic nitrile compound and the boiling point of water and lower than the boiling point of the aromatic amide compound.

4. The method for producing an aromatic nitrile compound according to claim 1, wherein the dehydration reaction is performed at a pressure of 2.7 kPa to 13.3 kPa.

5. The method for producing an aromatic nitrile compound according to claim 1, wherein a reaction solution of the dehydration reaction has a temperature that is 170° C. or higher and lower than 230° C.

6. The method for producing an aromatic nitrile compound according to claim 1, wherein the aromatic amide compound is selected from pyridine carboxamide or pyrazine amide, and the aromatic nitrile compound is selected from a corresponding cyanopyridine or cyanopyrazine.

7. The method for producing an aromatic nitrile compound according to claim 1, wherein the dehydration reaction uses a catalyst containing cesium.

8. A method for producing a carbonate ester, comprising:
   a first reaction step including a carbonate ester generation reaction of reacting one or more alcohol and carbon dioxide in the presence of an aromatic nitrile compound to generate a carbonate ester and water, and a hydration reaction of hydrating the aromatic nitrile compound with the generated water to generate an aromatic amide compound; and
   a second reaction step of, after the aromatic amide compound is separated from a reaction system of the first reaction step, regenerating the aromatic amide compound into the aromatic nitrile compound by a dehydration reaction of dehydrating the aromatic amide compound in the presence of diphenylether;

wherein at least a part of the aromatic nitrile compound regenerated in the second reaction step is used in the first reaction step.

9. The method for producing a carbonate ester according to claim 8, wherein the aromatic amide compound is selected from pyridine carboxamide or pyrazine amide, and the aromatic nitrile compound is selected from a corresponding cyanopyridine or cyanopyrazine.

10. The method for producing a carbonate ester according to claim 8, wherein the dehydration reaction uses a catalyst containing cesium.

11. The method for producing a carbonate ester according to claim 8, wherein the carbonate ester generation reaction uses a catalyst containing $CeO_2$.

12. The method for producing a carbonate ester according to claim 8, wherein the one or more alcohol has 1 to 6 carbons.

13. The method for producing a carbonate ester according to claim 8, wherein the first reaction step uses a solvent having a boiling point higher than the boiling point of the aromatic amide compound to be generated.

14. The method for producing a carbonate ester according to claim 8, wherein the solvent: contains at least one of a dialkylbenzene, an alkylnaphthalene, and a diphenylbenzene.

15. The method for producing a carbonate ester according to claim 8, wherein the dehydration reaction of dehydrating the aromatic amide compound is performed at a temperature of 170° C. or higher and lower than 230° C.

* * * * *